(12) United States Patent
Zhan et al.

(10) Patent No.: US 12,060,644 B2
(45) Date of Patent: Aug. 13, 2024

(54) CARBON DIOXIDE METHANATION AT LOW TEMPERATURE AND ELEVATED PRESSURE

(71) Applicant: Saudi Arabian Oil Company, Dhahran (SA)

(72) Inventors: Guodong Zhan, Dhahran (SA); Bodong Li, Dhahran (SA); Abdulwahab S. Aljohar, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 18/081,976

(22) Filed: Dec. 15, 2022

(65) Prior Publication Data

US 2024/0200204 A1 Jun. 20, 2024

(51) Int. Cl.
C25B 1/04 (2021.01)
C07C 1/12 (2006.01)
C25B 15/08 (2006.01)

(52) U.S. Cl.
CPC ............ *C25B 1/04* (2013.01); *C07C 1/12* (2013.01); *C25B 15/081* (2021.01)

(58) Field of Classification Search
CPC ............ C07C 1/12; C25B 1/04; C25B 15/081
See application file for complete search history.

(56) References Cited

U.S. PATENT DOCUMENTS

| | | | |
|---|---|---|---|
| 8,092,778 B2 | 1/2012 | Zhu | |
| 9,856,197 B2 | 1/2018 | Zubrin et al. | |
| 10,160,708 B2 | 12/2018 | Lee et al. | |
| 2009/0208403 A1 | 8/2009 | Hussain et al. | |
| 2012/0037363 A1 | 2/2012 | Curole | |
| 2013/0109888 A1 | 5/2013 | Moon et al. | |
| 2014/0357901 A1 | 12/2014 | Kooijman | |
| 2018/0086984 A1* | 3/2018 | Chen .................. B01J 23/10 | |
| 2018/0155261 A1 | 6/2018 | Raterman | |

(Continued)

FOREIGN PATENT DOCUMENTS

| | | |
|---|---|---|
| CN | 107376918 | 11/2017 |
| CN | 111017875 | 4/2020 |
| CN | 112705208 | 4/2021 |

(Continued)

OTHER PUBLICATIONS als.lbl.gov [online], "An Atomic-Level Understanding of Copper-Based Catalysts," Lawrence Berkley National Laboratory, May 2016, retrieved on Aug. 4, 2023, retrieved from URL <https://als.lbl.gov/an-atomic-level-understanding-of-copper-based-catalysts/>, 6 pages.

(Continued)

*Primary Examiner* — Jafar F Parsa
(74) *Attorney, Agent, or Firm* — Fish & Richardson P.C.

(57) ABSTRACT

An integrated carbon dioxide methanation system and a method of making methane are provided. An exemplary method of making methane includes generating electricity using renewable energy sources, obtaining carbon dioxide from biogas processing or post combustion carbon capture, obtaining hydrogen from water splitting or gasification of biomass, combining the carbon dioxide and the hydrogen to form a mixture, and reacting the mixture with a nickel catalyst made using atomic layer deposition to yield methane.

13 Claims, 5 Drawing Sheets

(56) References Cited

U.S. PATENT DOCUMENTS

| | | |
|---|---|---|
| 2022/0089442 A1 | 3/2022 | Zarabian et al. |
| 2023/0347321 A1 | 11/2023 | Alhajri et al. |

FOREIGN PATENT DOCUMENTS

| | | |
|---|---|---|
| CN | 113929054 | 1/2022 |
| JP | 2000169411 | 6/2000 |
| WO | WO 2013181045 | 12/2013 |
| WO | WO 2021152614 | 8/2021 |

OTHER PUBLICATIONS

Chen et al., "Rational Design of Novel Catalysts with Atomic Layer Deposition for the Reduction of Carbon Dioxide," Advanced Energy Materials, 2019, 9:1900889-1900889, 26 pages.

Giglio et al., "Integration between biomass gasification and high-temperature electrolysis for synthetic methane production," Biomass and Bioenergy, 2021, 148:106017-106029, 12 pages.

Khandan et al., "Direct production of dimethyl ether from synthesis gas utilizing bifunctional catalysts," Applied Petrochemical Research, 2012, 1:21-27, 7 pages.

Lv et al., "Recent Progresses in Constructing the Highly Efficient Ni Based Catalysts With Advanced Low-Temperature Activity Toward CO2 Methanation," Frontiers in Chemistry, Apr. 2020, 8(269):1-32, 32 pages.

Otaraku et al., "Process Design of Associated Natural Gas to Dimethyl Ether Production Via Direct Synthesis," International Journal of Chemical and Process Engineering Research, 2017, 5(1):1-7, 8 pages.

Rao et al., "Carbon Nanotubes and Related Nanomaterials: Critical Advances and Challenges for Synthesis toward Mainstream Commercial Applications," ACS Nano, 2018, 12:11756-11784, 29 pages.

International Search Report and Written Opinion in International Appln. No. PCT/US2023/083531, dated Mar. 28, 2024, 12 pages.

International Search Report and Written Opinion in International Appln. No. PCT/US2023/084075, dated Apr. 17, 2024, 16 pages.

International Search Report and Written Opinion in International Appln. No. PCT/US2023/084090, dated Apr. 24, 2024, 18 pages.

Lin et al., "Vertically Aligned Carbon Nanotubes for Thermal Interface Materials: Quality Control, Alignment Improvement and Laser Flash Measurement," 2010 Proceedings 60th Electronic Components and Technology Conference (ECTC), Jun. 1-4, 2010, pp. 967-972, 6 pages.

Lin et al., "Vertically Aligned Carbon Nanotubes on Copper Substrates for Applications as Thermal Interface Materials: from Synthesis to Assembly," 2009 Electronic Components and Technology Conference, May 26-29, 2009, pp. 441-447, 7 pages.

Wang et al., "Exergy analysis of methane cracking thermally coupled with chemical looping combustion for hydrogen production," Applied Energy, Apr. 15, 2016, 168: 1-12, 12 pages.

\* cited by examiner

CARBON DIOXIDE METHANATION AT LOW TEMPERATURE AND ELEVATED PRESSURE

TECHNICAL FIELD

This disclosure is directed to the conversion of carbon dioxide to methane at low temperature and elevated pressure using nickel-based catalysts and renewable energy sources.

BACKGROUND

Natural gas supplies 22% of the energy used worldwide, and makes up nearly a quarter of electricity generation. Further, natural gas is an important feedstock for the petrochemicals industry. According to the International Energy Agency (IEA), the worldwide consumption of natural gas is projected to increase from 120 trillion cubic feet (Tcf) in the year 2012 to 203 Tcf by the year 2040.

The recycling and utilization of carbon dioxide ($CO_2$) is gaining interest in fighting global warming. The concept of treating $CO_2$ not as a waste or contaminant, but rather as an opportunity, may prove promising for the future of producing cleaner fuels as well as producing useful materials and chemicals.

SUMMARY

An embodiment described in examples herein provides a method of making methane. The method includes generating electricity using renewable energy sources, obtaining carbon dioxide from biogas processing or post combustion carbon capture, and obtaining hydrogen from water splitting or gasification of biomass. The carbon dioxide and the hydrogen are combined to form a mixture. The mixture is reacted with a nickel catalyst made using atomic layer deposition to yield methane.

Another embodiment described in examples herein provides an integrated carbon dioxide methanation system. The integrated carbon dioxide methanation system includes a catalytic reactor including one or more nickel catalysts made using atomic layer deposition and a carbon dioxide source fluidically coupled to the catalytic reactor. The carbon dioxide source obtains carbon dioxide from biogas or post combustion carbon capture. A hydrogen source is fluidically coupled to the catalytic reactor. The hydrogen source obtains hydrogen from water splitting or gasification of biomass. An electrical source is electrically coupled to the catalytic reactor, the carbon dioxide source, and the hydrogen source. The electrical source generates electricity using renewable energy sources.

DETAILED DESCRIPTION

This disclosure relates to a carbon dioxide ($CO_2$) methanation process for biogas upgrading to renewable natural gas (RNG, i.e., methane, also called biomethane) using a catalytic reactor at low temperatures (e.g., in a range of about 200° C. to about 350° C.) and elevated pressures (in a range of about 5 bar to about 20 bar). The system is designed for continuous biogas upgrading (e.g., greater than 500 hours of continuous operation.) The catalytic reactor employs a nickel-based catalyst made using atomic layer deposition to catalyze the methanation reaction.

Methanation reaction. The methanation of carbon dioxide is an exothermic catalytic reaction given by Eq. 1:

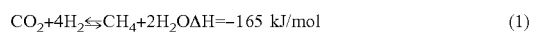

$$CO_2 + 4H_2 \leftrightharpoons CH_4 + 2H_2O \Delta H = -165 \text{ kJ/mol} \qquad (1)$$

Figure 1:
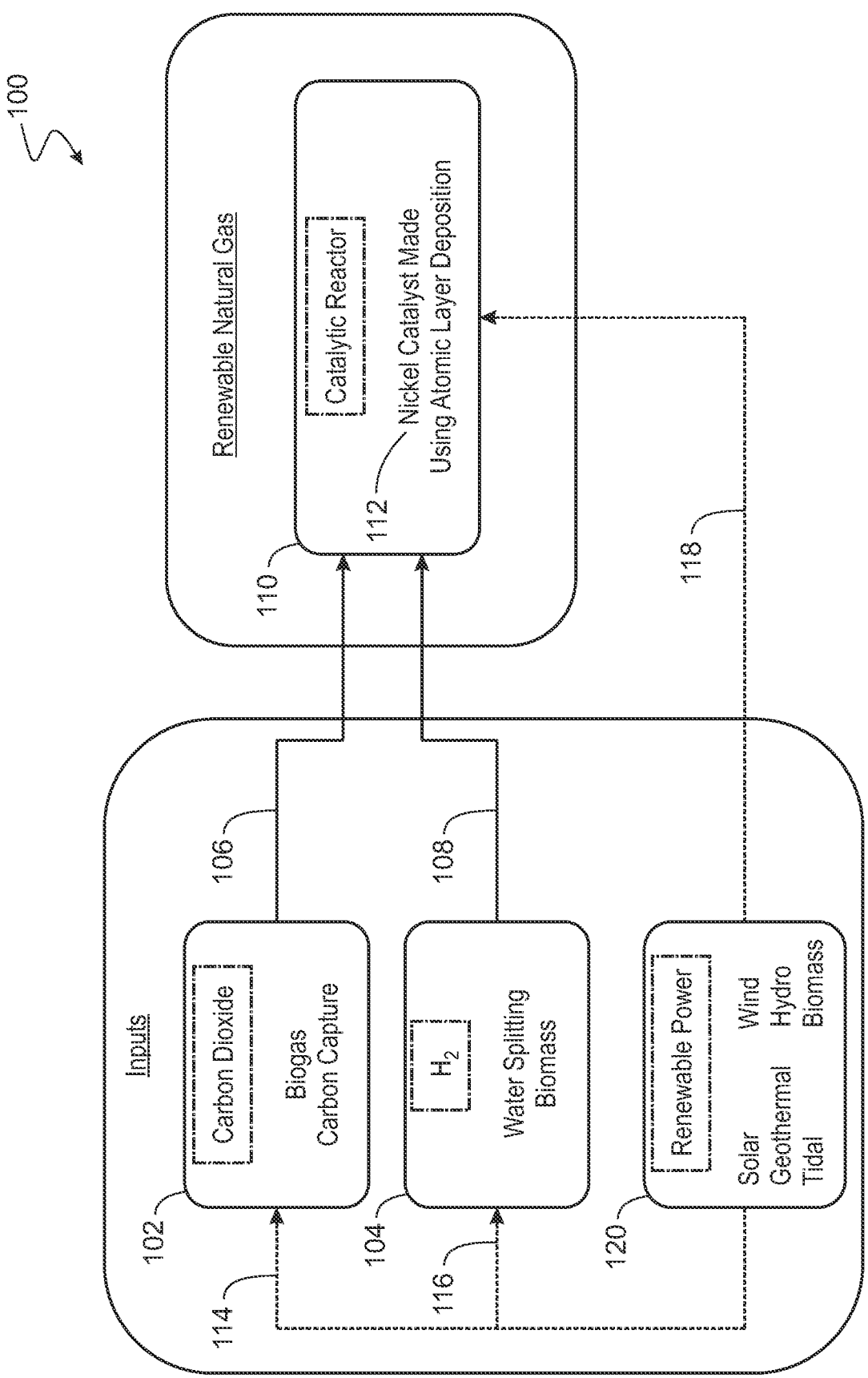
FIG. 1 a schematic drawing of a system 100 for the production of renewable natural gas using sustainable sources for the $CO_2$, $H_2$, and power necessary to produce the reactants and run the reactor.

FIG. 1 is a schematic drawing of a system 100 for the production of renewable natural gas using sustainable sources for the $CO_2$, $H_2$, and power necessary to produce the reactants and run the reactor. Carbon dioxide 102 generated from environmentally sustainable processes (e.g., biogas processing and carbon capture) and hydrogen gas 104 produced using water splitting and biomass processing are provided in fluid streams 106 and 108, respectively to a catalytic reactor 110 for the production of methane by the catalytic reaction given by Eq. 1. The catalytic reactor 110 uses a nickel catalyst 112 made using atomic layer deposition to catalyze the methanation reaction. The electricity used for the production of carbon dioxide 114, the production of hydrogen 116, and the operation of the catalytic reactor 118 is provided by renewable power sources 120 including solar, wind, geothermal, hydro, tidal, and biomass. The system 100 recycles a greenhouse gas $CO_2$ and converts it into renewable natural gas energy source (i.e., methane) using energy derived from renewable sources (biomass, biogas, solar, wind, geothermal, hydro, and tidal).

The methanation reaction given by Eq. 1 can be catalyzed using metal catalysts. The nickel catalysts disclosed herein can catalyze the reaction at low temperature (e.g., in a range of about 200° C. to about 350° C.) which reduces the power 120 used to produce the renewable natural gas and increases the efficiency of system 100.

Carbon dioxide production. Carbon dioxide can be obtained through the processing of biogas made from a wide range of biomass feedstocks. These biomass feedstocks include: agricultural residues derived from field activities after harvesting the main product, e.g. straw, prunings, corn stover, etc., as well as animal manure; forest biomass including residues from harvest operations that are left in the forest following stem wood removal, e.g. branches, foliage, roots etc. and complementary fellings; energy crops including annual or perennial crops specifically bred and cultivated to produce biomass with specific traits; household biowaste streams including mainly kitchen and garden waste, paper and cardboard, but including a proportion of other waste fractions which are of biological origin; construction/demolition wood including wood offcuts from building construction and wood recovered during demolition; packaging, waste wood, e.g. palettes, crates, etc.; household waste wood including old furniture, fencing; market waste including green tops and unsold vegetables from markets; sewage sludge, food processing wastes including wastes from the dairy and sugar industry, wine and beer production; waste streams with lower volumes involved (e.g., orange zests from orange juice production); gardening wastes including grass cuttings, leaves and small branches; algae/aquaculture including microalgae (microorganisms) and macroalgae, such as seaweed; and marine biomass.

Post combustion carbon capture can be used to isolate $CO_2$ from industrial sources such as power plant flue gas streams. In one example, post combustion carbon capture is achieved in a multistep process. The steps include cooling the flue gas, removing sulfur dioxide and fine particles and aerosols from the gas stream, and separating the $CO_2$ using a liquid aqueous amine absorber column. The solution enters a desorber column in which the $CO_2$ is stripped out of the amine solution. The $CO_2$ stream saturated with water leaves the desorber column and is cooled in a condenser. The condensate and $CO_2$ rich gas are separated in a reflux drum and the condensate is fed back to the desorber column. The $CO_2$ rich gas can then be stored and sent to the catalytic reactor for the production of renewable natural gas.

Hydrogen production. Renewable hydrogen gas can be derived from sustainable materials using water as source. The water splitting reaction is given by Eq. 2:

$$2H_2O \rightarrow 2H_2 + O_2 \quad \Delta H = 285 KJ/mol \qquad (2)$$

Methods for making hydrogen from water include electrocatalytic water splitting, photocatalytic water splitting, and thermally driven reactions on reducible oxides. Electrocatalytic methods use electrodes immersed in an aqueous medium for the reduction of hydrogen at the cathode and the oxidation of oxygen at the anode. In some cases, the technology is performed at neutral pH using noble metals for both electrodes, or in alkaline environments using electrodes made of mixed metal oxide based on Fe, Ni, and Co cations. The electricity used to drive the water splitting can be generated using photovoltaic cells, thus making the generation of the hydrogen gas renewable. In photocatalytic water-splitting, a semiconductor photocatalyst uses light energy, such as solar energy, to drive the water splitting reaction given Eq. 2. Thermal water splitting catalyzed by metal oxides uses the input of heat to generate oxygen vacancies in the metal oxides that then reduce the hydrogen in water to hydrogen gas.

Hydrogen gas can be generated renewably by the conversion of biomass and related hydrocarbon feedstocks using catalytic gasification and reforming technology. Gasification is a process that converts organic or fossil-based carbonaceous materials at high temperature, without combustion, with a controlled amount of oxygen and/or steam into carbon monoxide, hydrogen, and carbon dioxide. For example, for starch, gasification can be performed following Eq. 3.

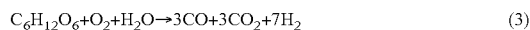

$$C_6H_{12}O_6 + O_2 + H_2O \rightarrow 3CO + 3CO_2 + 7H_2 \qquad (3)$$

The carbon monoxide can then react with water to form carbon dioxide and more hydrogen via a water-gas shift reaction shown in Eq. (4).

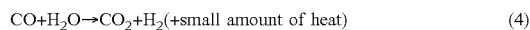

$$CO + H_2O \rightarrow CO_2 + H_2 (+\text{small amount of heat}) \qquad (4)$$

Adsorbers or membranes can separate the hydrogen from this gas stream. Pyrolysis is the gasification of biomass in the absence of oxygen. In general, biomass does not gasify as easily as coal, and it produces other hydrocarbon compounds in the gas mixture exiting the gasifier. This is especially true when no oxygen is used. As a result, typically an extra step can be taken to reform these hydrocarbons with a catalyst to yield a clean mixture of hydrogen, carbon monoxide, and carbon dioxide. Then, just as in the gasification process for hydrogen production, a water-gas shift reaction, using steam, converts the carbon monoxide to carbon dioxide. The hydrogen produced is then separated and purified.

Renewable power sources. The generation of carbon dioxide 102, the generation of hydrogen gas 104, and the generation of renewable natural gas in the catalytic reactor 110 uses the input of electricity 114, 116 and 118, respectively. This electricity is produced by renewable power source 120 using environmentally sustainable methods including solar, wind, geothermal, hydro, tidal, and processing of biomass.

Figure 2:
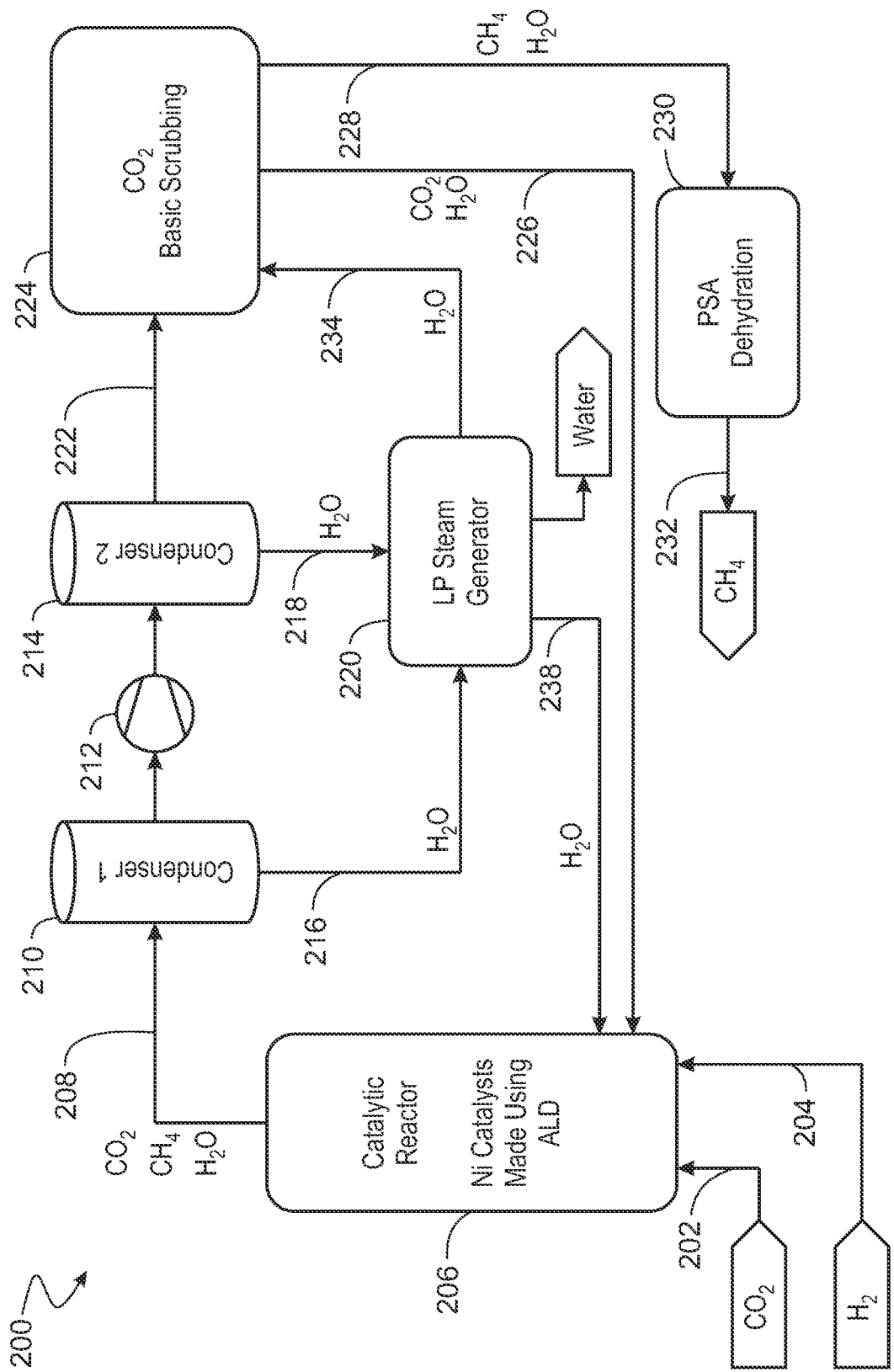
FIG. 2 depicts an example of an integrated carbon dioxide methanation plant 200 that uses recycling of carbon dioxide and water.

Carbon dioxide methanation plant. FIG. 2 depicts an example of an integrated carbon dioxide methanation plant 200 that uses recycling of carbon dioxide and water. The plant includes a multistage catalytic reactor using Ni-based catalysts to catalyze the methanation reaction given by Eq. 1. Streams of carbon dioxide 202 and hydrogen gas 204 obtained from renewable sources are fed into the catalytic reactor 206. The multistage catalytic reactor 206 includes a number of catalytic beds containing the nickel catalyst made using atomic layer deposition through which the carbon dioxide 202 and hydrogen gas 204 streams are passed. The number of catalytic beds can be in a range from 1 bed to 10 beds. The gas stream 208 exiting the catalytic reactor 206 includes carbon dioxide, water, and methane. Stream 208 passes through a first condenser 210, a compressor 212, and a second condenser 214. The water 216 and 218 removed by the condensers is fed into a low pressure (LP) steam generator 220. The product stream 222 exiting the second condenser 214 is fed into a $CO_2$ scrubbing unit 224 for separation of water and $CO_2$ from the methane stream. The $CO_2$ scrubbing unit 224 uses hot potassium carbonate to remove $CO_2$ from the product stream, which is then recycled 226 together with separated $H_2O$ back to the catalytic reactor 206. The product stream 228 exiting the $CO_2$ scrubbing unit 224 is fed into a pressure-swing adsorption (PSA) unit 230 for further removal of water from the product stream. The methane product 232 exits the PSA dehydration unit 230. The LP steam generator 220 reboils the recycled water 216 and 218 from condensers 210 and 214. The LP steam line 234 is reused in the $CO_2$ scrubbing unit for the separation of $CO_2$ from $CH_4$. LP steam line 238 is sent to catalytic reactor 206 where it is used in the separation of $CO_2$ and $H_2O$ from stream 226 originating from the $CO_2$ scrubbing unit. The recycled $CO_2$ obtained from stream 226 is added to stream 202 for conversion to $CH_4$ in the catalytic reactor 206.

Figure 3:
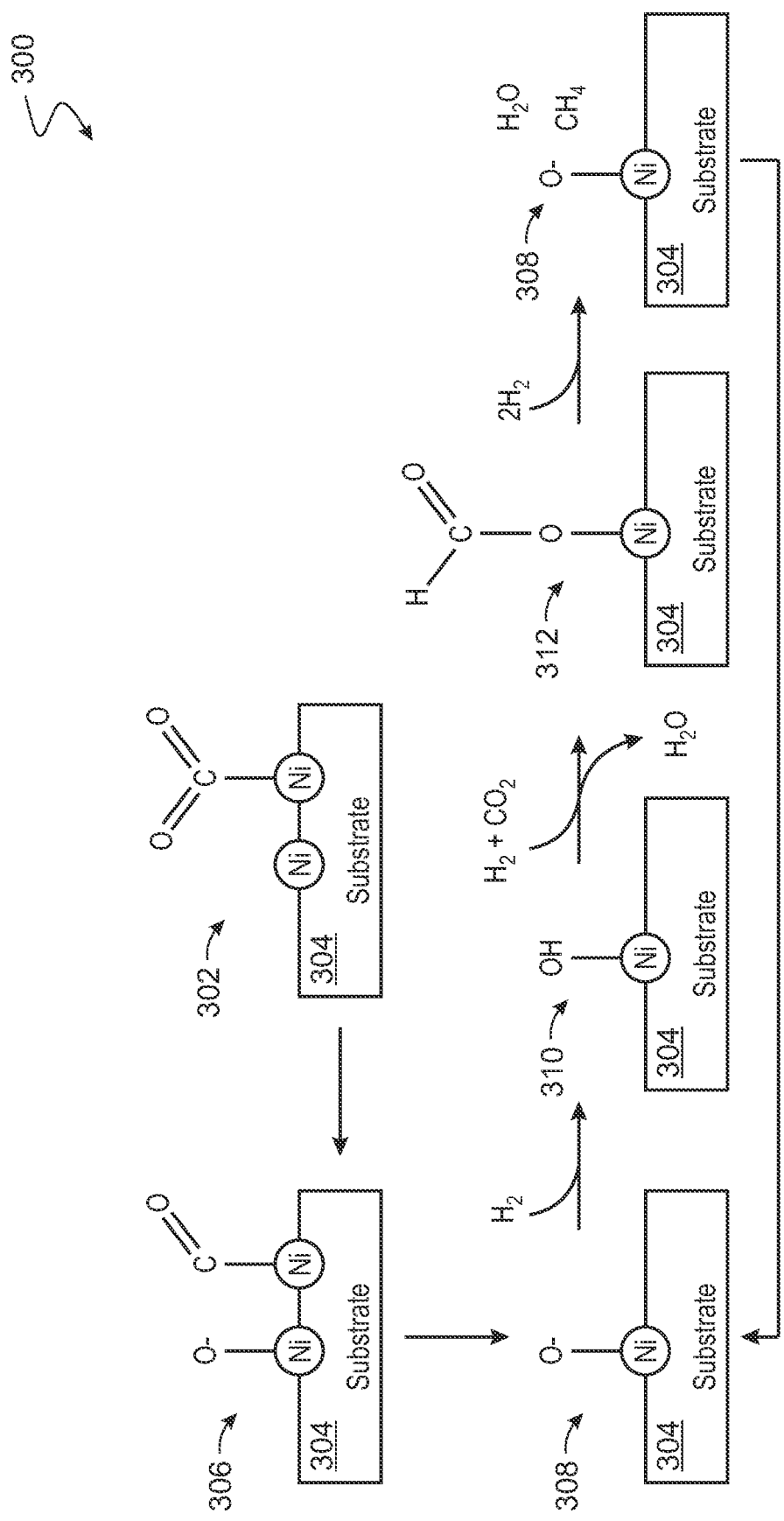
FIG. 3 depicts an example of a proposed mechanism 300 for the methanation of carbon dioxide using a nickel catalyst.

Nickel catalyst for carbon dioxide methanation. The mechanism for metal catalyzed methanation of carbon dioxide to methane is not well understood, and it is possible that multiple mechanisms are active simultaneously during the reaction. Without being bound by theory, FIG. 3 depicts an example of one proposed mechanism 300 for the methanation reaction using a nickel catalyst. Carbon dioxide adsorbs 302 on the nickel coated substrate 304 and dissociates into adsorbed carbon monoxide and an oxide species 306. Hydrogen gas is reduced by the oxide species 308 to form an adsorbed hydroxyl species 310. Hydrogen gas and carbon dioxide react with the adsorbed hydroxyl species to form a monodentate adsorbed formate species 312 with the loss of water. Hydrogen gas reacts with the adsorbed formate species 312 to form water and methane and regenerate the oxide species 308, which can then participate in another catalytic cycle. Other mechanism, for example, involving adsorbed carbon monoxide and formaldehyde, can also be involved in the methanation reaction.

Figure 4A:
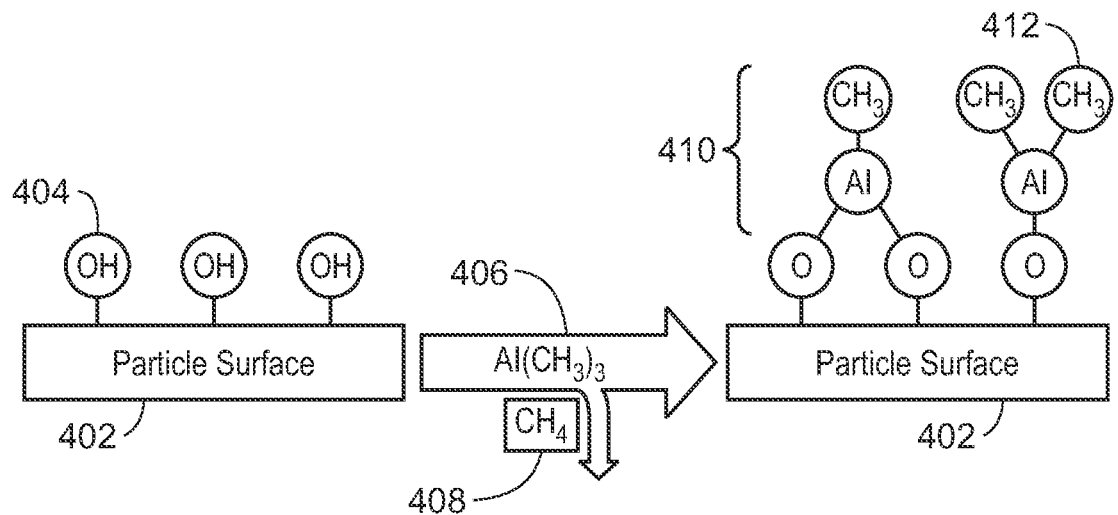
FIGS. 4A and 4B are drawings of the surface of the catalyst showing the deposition of atomic layers of alumina to form a catalyst.
Figure 4B:
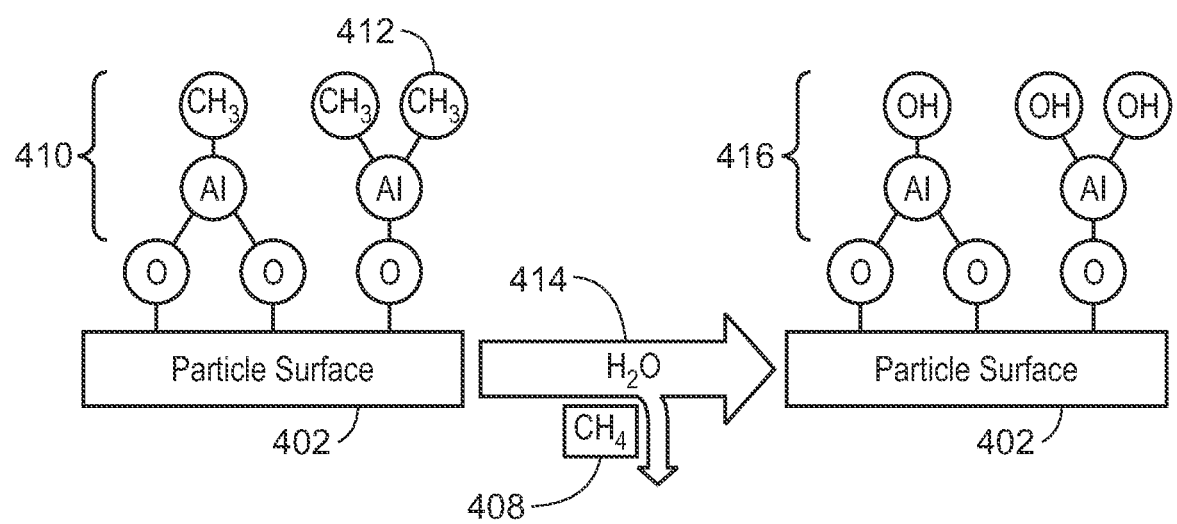

FIGS. 4A and 4B are drawings of the surface of the catalyst showing the deposition of atomic layers of alumina to form a catalyst. As shown in FIG. 4A, a catalyst support 402 has hydroxyl groups 404. In various embodiments, the catalyst support 402 is formed from silica, alumina, or another metal oxide. The catalyst support 302 may be a particulate or a solid surface of an interior of a tube.

In various embodiments, a particle is chosen from materials that lower catalyst costs, such as using a silica sand. The catalyst support 402 is treated by contact with an excess of trimethyl aluminum (TME), $Al(CH_3)_3$, 406. The TME 406 reacts with the hydroxyl groups 404, releasing methane 408, and forming a layer 410 over the catalyst support 402 that includes methyl groups 412 as the outer surface. The reaction is limited by the number of hydroxyl groups 404, first slowing, and then stopping as the hydroxyl groups 404 are exhausted. For example, the surface reaction may include 90% of the hydroxyl groups 404, 95%, 99%, or higher, depending on contact time.

FIG. 4B shows the second step of the reaction. After the TMA treatment, the catalyst support 402 is further treated by contact with an excess of water 414. The water 414 reacts with the methyl groups 412, releasing further methane 408, and forming a layer of alumina 416 over the catalyst support 402. As for the reaction in FIG. 4A, the reaction in FIG. 4B is limited by the number of methyl groups 412, first slowing, and then stopping as the methyl groups 412 are exhausted. As this is a very active reaction, most, or all, of the methyl groups 412 will be displaced. The surface reaction may include 95% of the methyl groups 412, 99%, or higher, depending on contact time. The reactions in FIGS. 4A and 4B may be iterated to form additional layers over the catalyst support 402, such as one layer of alumina 416, two layers of alumina 416, three layers of alumina 416, or more. For a catalyst support 402 in a particulate form, the iteration of the procedure described by FIGS. 4A and 4B produces a coated particle.

If the catalyst support 402 is a particulate, the reactions shown in FIGS. 4A and 4B can be performed in a fluidized bed reactor or a rotary reactor, among others. Once the desired number of layers has been deposited, other catalysts may be deposited over the alumina surface of the coated particle, such as copper oxide/zinc oxide, nickel, platinum, palladium, or ruthenium, or other metals as described herein. In some embodiments, the additional metals are deposited by mixing the coated particles with a solution of the target metal as a salt, then drying the solution, and calcining to form the final catalyst.

For example, to form a catalyst with nickel domains, the catalyst support 402 can be treated by immersion in a solution of a nickel salt, such as solution of nickel nitrate. The catalyst support 402 is then removed from the solution, or, for a particulate, the solution is drained from the reactor. The catalyst support 402 is then dried, for example, being heated at a temperature of between 50° C. and 100° C., or at a temperature of less than about 100° C. After drying, the catalyst support may be calcined at a higher temperature, such as between 500° C. and 700° C. A reducing atmosphere, such as a mixture of nitrogen and hydrogen, is used to reduce the nickel to the metallic form, producing nickel metal domains over the surface. The size of the domains may be controlled by the amount of the nickel solution used, and the number of repetitions of the treatment with the solution. In some embodiments, a continuous film is formed by multiple cycles of addition of the solution, each followed by treatment in a reducing atmosphere. Similar processes may be used to add domains of other metals, such as cobalt, platinum, palladium, ruthenium, and the like. If the catalyst support 402 is a particulate, the treatment with the solution may be performed with the particulates in a fluidized state, wherein the metal salt solution is entrained with the gas use for the fluidization.

Figure 5:
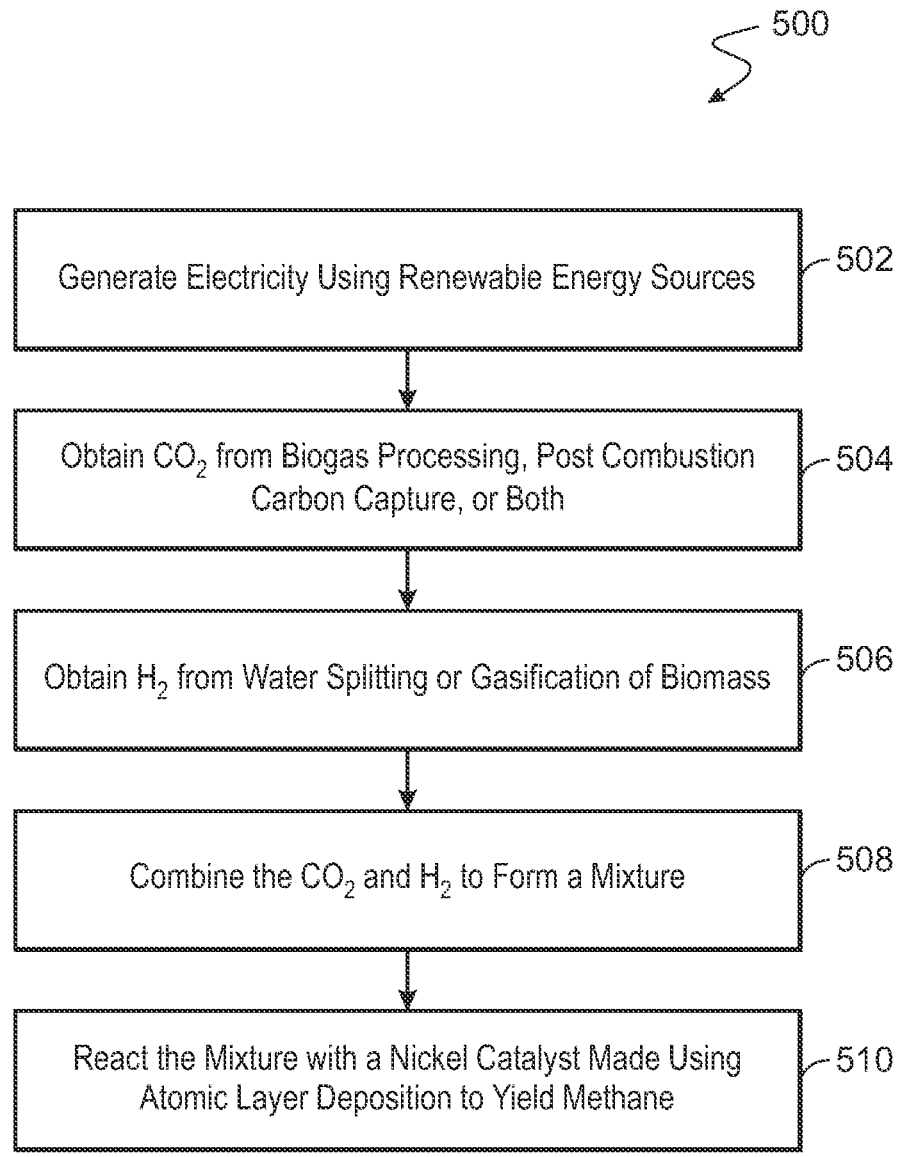
FIG. 5 shows a process for making methane 500 (i.e., renewable natural gas).

FIG. 5 shows a process for making methane 500 (i.e., renewable natural gas). Electricity is generated from renewable energy sources in 502, including biomass, biogas, solar, wind, geothermal, hydro, and tidal. In 504, carbon dioxide is obtained from biogas processing, post combustion carbon capture, or both. In 506, hydrogen in obtained from water splitting or gasification of biomass. In 508, the carbon dioxide and hydrogen are combined to form a mixture. In 510, the mixture is reacted with a nickel catalyst made using atomic layer deposition to yield methane.

Embodiment 1 provides a method of making methane. The method includes generating electricity using renewable energy sources, obtaining carbon dioxide from biogas processing or post combustion carbon capture, and obtaining hydrogen from water splitting or gasification of biomass. The carbon dioxide and the hydrogen are combined to form a mixture. The mixture is reacted with a nickel catalyst made using atomic layer deposition to yield methane.

Embodiment 2 is a method of embodiment 1, wherein reacting the mixture with the nickel catalyst made using atomic layer deposition includes heating the mixture at temperature in a range of about 200° C. to about 350° C. at a pressure in a range of about 5 bar to about 20 bar.

Embodiment 3 is a method of embodiment 1 or 2, wherein the renewable energy sources include solar, wind, geothermal, hydro, tidal, and processing of biomass.

Embodiment 4 is a method of any one of embodiments 1 through 3, wherein the biogas is obtained from biomass.

Embodiment 5 is a method of embodiment 4, wherein the biomass includes one or more of agricultural residue, forest residue, energy crops, household biowaste, construction and demolition wood, sewage sludge, food processing wastes, gardening wastes, algae, or marine biomass.

Embodiment 6 is a method of any one of embodiments 1 through 5, wherein the post combustion carbon capture includes isolating the carbon dioxide from flue gas streams.

Embodiment 7 is a method of any one of embodiments 1 through 6, wherein the water splitting includes electrolytic water splitting, photocatalytic water splitting, or thermally driven reactions on reducible oxides.

Embodiment 8 is a method of any one of embodiments 1 through 7, wherein the gasification of biomass includes pyrolysis of biomass in the absence of oxygen.

Embodiment 9 is a method of any one of embodiments 1 through 8, wherein the nickel catalyst includes particles of silica, alumina, or another metal oxide.

Embodiment 10 is a method embodiment 9, wherein the nickel catalyst includes one or more layers of alumina deposited on the particles using atomic layer deposition.

Embodiment 11 is method of embodiment 10, wherein the nickel catalyst includes nickel metal domains deposited over the one or more layers of alumina.

Embodiment 12 is a method of embodiment 11, wherein the nickel catalyst further includes domains of cobalt, platinum, palladium, ruthenium, and the like.

Embodiment 13 provides an integrated carbon dioxide methanation system. The integrated carbon dioxide methanation system includes a catalytic reactor including one or more nickel catalysts made using atomic layer deposition and a carbon dioxide source fluidically coupled to the catalytic reactor. The carbon dioxide source obtains carbon dioxide from biogas or post combustion carbon capture. A hydrogen source is fluidically coupled to the catalytic reactor. The hydrogen source obtains hydrogen from water splitting or gasification of biomass. An electrical source is electrically coupled to the catalytic reactor, the carbon dioxide source, and the hydrogen source. The electrical source generates electricity using renewable energy sources.

Embodiment 14 is a system of embodiment 13, wherein the nickel catalyst includes particles of silica, alumina, or another metal oxide.

Embodiment 15 is a system of embodiment 14, wherein the nickel catalyst includes one or more layers of alumina deposited on the particle using atomic layer deposition.

Embodiment 16 is a system of embodiment 15, wherein the nickel catalyst includes nickel metal domains deposited over the one or more layers of alumina.

Embodiment 17 is a system of embodiment 16, wherein the nickel catalyst further includes domains of cobalt, platinum, palladium, ruthenium, and the like deposited over the one or more layers or alumina.

Other implementations are also within the scope of the following claims.

What is claimed is:

1. A method of making methane, the method comprising:
generating electricity using renewable energy sources;
obtaining carbon dioxide from biogas processing or post combustion carbon capture;
obtaining hydrogen from water splitting or gasification of biomass;
combining the carbon dioxide and the hydrogen to form a mixture; and
reacting the mixture with a nickel carbon dioxide methanation catalyst to yield methane, wherein the nickel carbon dioxide methanation catalyst comprises particles of silica, alumina, or another metal oxide, and one or more layers of alumina deposited on the particles using atomic layer deposition.

2. The method of claim 1, wherein reacting the mixture with the nickel carbon dioxide methanation catalyst comprises heating the mixture at a temperature in a range of about 200° C. to about 350° C. at a pressure in a range of about 5 bar to about 20 bar.

3. The method of claim 1, wherein the renewable energy sources comprise solar, wind, geothermal, hydro, tidal, and processing of biomass.

4. The method of claim 1, wherein the biogas is obtained from biomass.

5. The method of claim 4, wherein the biomass comprises one or more of agricultural residue, forest residue, energy crops, household biowaste, construction and demolition wood, sewage sludge, food processing wastes, gardening wastes, algae, or marine biomass.

6. The method of claim 1, wherein the post combustion carbon capture comprises isolating the carbon dioxide from flue gas streams.

7. The method of claim 1, wherein the water splitting comprises electrolytic water splitting, photocatalytic water splitting, or thermally driven reactions on reducible oxides.

8. The method of claim 1, wherein the gasification of biomass comprises pyrolysis of biomass in the absence of oxygen.

9. The method of claim 1, wherein the nickel carbon dioxide methanation catalyst comprises nickel metal domains deposited over the one or more layers of alumina.

10. The method of claim 9, wherein the nickel catalyst further comprises domains of cobalt, platinum, palladium, or ruthenium deposited over the one or more layers of alumina.

11. An integrated carbon dioxide methanation system, the system comprising:
a catalytic reactor comprising one or more nickel carbon dioxide methanation catalysts comprising particles of silica, alumina, or another metal oxide, and one or more layers of alumina deposited on the particles using atomic layer deposition;
a carbon dioxide source fluidically coupled to the catalytic reactor, wherein the carbon dioxide source obtains carbon dioxide from biogas or post combustion carbon capture;
a hydrogen source fluidically coupled to the catalytic reactor, wherein the hydrogen source obtains hydrogen from water splitting or gasification of biomass; and
an electrical source electrically coupled to the catalytic reactor, the carbon dioxide source, and the hydrogen source, wherein the electrical source generates electricity using renewable energy sources.

12. The system of claim 11, wherein the nickel carbon dioxide methanation catalyst comprises nickel metal domains deposited over the one or more layers of alumina.

13. The system of claim 12, wherein the nickel carbon dioxide methanation catalyst further comprises domains of cobalt, platinum, palladium, or ruthenium deposited over the one or more layers of alumina.

* * * * *